United States Patent
Bartholeyns et al.

(10) Patent No.: US 6,596,275 B1
(45) Date of Patent: *Jul. 22, 2003

(54) MONOCYTE DERIVED CELLS WITH IMMUNOSUPPRESSIVE PROPERTIES, PROCESS FOR THEIR PREPARATION AND THEIR USES IN PHARMACEUTICAL COMPOSITIONS

(75) Inventors: Jacques Bartholeyns, Bures-sur-Yvette (FR); Mohamed Chokri, Paris (FR); Jean-Loup Romet-Lemonne, Paris (FR)

(73) Assignee: I.D.M. Immuno-Designed Molecules, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/647,532

(22) PCT Filed: Mar. 29, 1999

(86) PCT No.: PCT/EP99/02107

§ 371 (c)(1),
(2), (4) Date: Oct. 2, 2000

(87) PCT Pub. No.: WO99/50394

PCT Pub. Date: Oct. 7, 1999

(30) Foreign Application Priority Data

Mar. 30, 1998 (EP) ............................................. 98400743

(51) Int. Cl.$^7$ ........................... A01N 63/00; C12N 5/08; C12N 5/10
(52) U.S. Cl. .................................... 424/93.71; 435/372
(58) Field of Search ........................ 424/93.71; 435/372

(56) References Cited

U.S. PATENT DOCUMENTS

| | | | |
|---|---|---|---|
| 4,608,255 A | | 8/1986 | Kahn et al. |
| 4,952,812 A | | 8/1990 | Miripol et al. |
| 5,599,920 A | * | 2/1997 | Patel et al. |

FOREIGN PATENT DOCUMENTS

| | | |
|---|---|---|
| EP | 0 138 489 | 4/1985 |
| WO | WO 96/22781 | 8/1996 |

OTHER PUBLICATIONS

Fujihara et al., Decreased Inducible Expression of CD80 and CD86 in Human Monocytes After Ultraviolet–B Irradiation: Its Involement in Inactivation of Allogenecity, Mar. 15, 1986, Blood 87(6): 2386–2393.*

Cameron et al., Relationship of the Suppression of Macrophage Mediated Tumor Cytotoxicity in Conjunction with Secretion of Prostagladin from the macrophages of breast cancer patients, 1982, Int J. Immunopharmaco 4(5): 445–50.*

Mulders et al., Highly efficient and consistent gene transfer into dendritic cells utilizing a combination of ultraviolet–irradiated adenovirus and poly(L–lysine) conjugates, Mar. 1, 1998, Cancer Res 58(5):956–61.*

Arthur et al (Cancer Gene Therapy 4(1): 14–25, 1997/.*

Webster's II New Riverside University Dictionary, p. 1131, 1994.*

H. Wolf et al, control by pulse parameters of electric field–mediated gene tranfer in mammalian cells, *Biophysical Journal*, vol. 66, 1994, pp. 524–531.

S. Sixou et al., "Specific electopermeabilization of leucocytes in a blood sample and application to large volumes of cells", *Biochimica Biophysica ACTA*, vol. 1028, 1990, pp. 154–160.

K. Urano et al., "PUVA suppresses the expresion of cell adhesion molecules of lymphocytes", *Exp. Dermatol.*, vol. 4, 1995, pp. 36–41.

H. Yagi et al., "TCVR beta7 Th2 cell mediate UVB–induced suppression of murine contact photsensitivity by releasing IL–10", *Journal of Immunology*, vol. 156, No. 4, 1996, pp. 1824–1831.

I. Kremer et al., "Reduced IL–2 production by monocytes upon UVB irradiation selectively limits activation of T helper–1 cells", *Journal of Immunology*, vol. 157, 1996, pp. 1913–1918.

S.E.Ulrich, "Mechanism involved in the systemic suppression of antigen–presenting cell function by UV–irradiation", *Journal of Immunology*, vol. 152, 1994, pp. 3410–3416.

J.M. Rivas et al., "Systemic suppression of delayed–type hypersensitivity by supernatants from UV–irradiated keratinocytes", *Journal of Immunology*, vol. 149, No. 12, 1992, pp. 3865–3871.

A.A. El–Ghorr et al., "The role of IL–4 in UVB light induced immunosuppression", *Immunology*, vol. 92, 1997, pp. 26–32.

S.W. Yasumoto et al., "UVB irradiation alters cytokine production by immune lymphocytes in herpers simplex virus infected mice", *Journal of Dermatological Science*, vol. 8, 1994, pp. 218–223.

* cited by examiner

*Primary Examiner*—Christina Chan
*Assistant Examiner*—Phuong N. Huynh
(74) *Attorney, Agent, or Firm*—Young & Thompson

(57) ABSTRACT

Monocyte derived cells with immunosuppressive properties including an increase in at least one of the following PGE-2, IL-10 and IL-4. Monocyte derived cells with a decreased level of expression and secretion of inflammatory and immunostimulating cytokines and a decrease on the membrane of activation or accessory molecules in the presence of polylysine-cDNA in the nucleus of the monocyte derived cells.

8 Claims, No Drawings

MONOCYTE DERIVED CELLS WITH IMMUNOSUPPRESSIVE PROPERTIES, PROCESS FOR THEIR PREPARATION AND THEIR USES IN PHARMACEUTICAL COMPOSITIONS

This application is a 371 of PCT/EP99/02107 filed Mar. 29, 1999, and European patent EPO 894007435, filed on Mar. 30, 1998.

The invention relates to suppressive monocyte derived cells, a process for their preparation, and their uses in pharmaceutical compositions.

It is known, that macrophages, or other cells derived from monocytes or from their precursors, with their strong capacity for endocytosis, digestion, and surface antigen presentation, are capable of controlling the immune response.

Monocytes derived cells (MDCs) are immune cells such as obtained by culture of blood mononuclear cells in non adherent gas permeable plastic or Teflon bags for 5 to 10 days at 37° C. in $O_2/CO_2$ atmosphere. Their culture medium (RPMI, IMDM, AIM5 (Gibco) or X-VIVO (Biowhittaker)) contains eventually cytokines or ligands as defined in patents PCT/EP93/01232, WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159:29–38, 1993);

"Immune therapy with macrophages: Present status and critical requirements for implementation" (Bartholeyns J., Romet-Lemonne J-L., Chokri M., Lopez M.; Immunobiol., 195:550–562, 1996);

"Dendritic cells can present antigen in vivo in a tolerogenic or immunogenic fashion" Finkelman, Lees, Birnbaum et al., J. Immunology, 157:1406–1414, 1996;

"Dendritic cells as adjuvants for immune-mediated resistance to tumors" (Schuler G. and Steinman R. M.; J. Exp. Med., 186:1183–1187, 1997). All these patents applications and articles are included herein for references.

They can be centrifuged to be concentrated and purified before resuspension in isotonic solution.

Monocytes derived cells (MDCs) can either be macrophages, phagocytozing cells, growth factors and cytokine releasing cells, or dendritic cells according to their conditions of differentiation. Dendritic cells can for example be obtained as described in "Dendritic cells can present antigen in vivo in a tolerogenic or immunogenic fashion" Finkelman, Lees, Birnbaum et al., J. Immunology, 157:1406–1414, 1966 and "Dendritic cells as adjuvants for immune-mediated resistance to tumors" (Schuler G. and Steinman R. M.; J. Exp. Med., 186:1183–1187, 1997), and EP 97/02703.

In physiology, monocyte derived cells are called initially to induce an immune response.

In a normal situation, this immune response has to be stopped in order to avoid a pathological enhanced response, and this control is mediated, in the body, by monocyte derived cells which have not yet been completely identified and are not yet mastered in ex vivo conditions.

One of the aims of the invention is to provide suppressed monocyte derived cells which present the properties of controlling the immune response, when compared to normal monocyte derived cells described until now.

Another aim of the invention is provide a process for the preparation of said suppressive monocyte derived cells.

Another aim of the invention is to provide new pharmaceutical compositions containing said suppressive monocyte derived cells.

Another aim of the invention is to provide new methods for inducing inmmunotolerance.

Another aim of the invention is to provide new methods for treating autoimmune diseases.

Another aim of the invention is to provide new methods for the treatment of chronic inflammations.

Another aim of the invention is to provide new methods for the treatment of allogenic graft rejection.

Another aim of the invention is to provide new methods for gene therapy.

The invention relates to suppressive monocyte derived cells presenting the following characteristics:

1) increased release, with respect to normal monocyte derived cells, of at least one of the following compounds:
   PGE-2
   IL-10
   IL-4
   and decreased level of expression and secretion of inflammatory and immunostimulating cytokines such as IL-1, IL-12, IFNγ, with respect to normal monocytes derived cells,
   and decreased presence, on their membrane, with respect to normal monocyte derived cells, of at least one of the following activation or accessory molecules such as CD80, CD86, and CD40,
   and/or 2) presence in their nucleus of at least one exogenous nucleic acid which has been integrated in the absence of the monocyte derived cell division.

The expression "normal monocyte derived cells" corresponds to monocytes cultured in defined media or in the presence of cytokines which present MHCI and MHCII molecules at their surfaces, release cytokines and growth factors, induce proliferation of lymphocytes in mixed lymphocyte reaction assays.

Normal monocyte derived cells can be obtained for instance from blood derived monocytes purified and cultured in the presence of GM-CSF and other cytokines.

Monocyte derived cells properly stimulated can trigger the immune system leading to T-cell activation and production of antibodies. In contrast, monocyte derived cells which do not present costimulatory signals on their membranes and release suppressive cytokines (e.g. TGF-β) or cytokines inducing a TH2 response (e.g. IL-4, IL-10) or suppressive factors (e.g. PGE2) do inhibit the immune system. If such monocyte derived cells have interiorized and processed antigens of interest, they can specifically induce peripheral tolerance, with durable antigen specific unresponsiveness in the absence of generalized inununosuppression.

According to an advantageous embodiment of the invention, the increased release, with respect to normal monocyte derived cells, of at least one of the following compounds:
prostaglandins such as PGE-2
arachidonic acid metabolites
TGF-β
IL-10
IL-4
is in an amount higher than 0.1 pg/cell/hr.

This can be measured by ELISA method.

According to an advantageous embodiment of the invention, decreased level, with respect to normal monocyte derived cells, of expression and of secretion of inflammatory and immunostimulating cytokines such as IL-1, IL-12, IFNγ, is below 0.01 pg/cell/hr.

This can be measured by ELISA methods.

According to another embodiment of the invention, the decreased presence, with respect to normal monocyte derived cells, on their membrane of at least one of the following activation or accessory molecules such as CD80, CD86, CD1a and adhesins such as CD40 or ICAM, MHCI and MHCII molecules is in an amount of less than about $10^3$ molecules/cell, as measured by flow cytometry.

According to another embodiment of the invention, the decreased phagocytosis capacity, with respect to normal monocyte derived cells is in the average of less than 5 particles of yeast phagocytosed in one hour.

In a particular embodiment of the invention, the monocyte derived cells as described above, contain exogenous compounds in their cytoplasm such as drugs, protein, growth factors of interest.

In another embodiment, the monocyte derived cells as described above contain in their cytoplasm exogenous DNA coding for a protein of interest.

It should be made clear that depending upon the conditions in which the monocyte derived cells are preferred and more particularly depending upon the nature of the physical stress to which the monocyte derived cells of the invention are submitted, as explained hereafter, either the DNA contained in the cytoplasm of said monocyte derived cells remain in the cytoplasm after the physical stress, or there is an uptake of said exogenous DNA by their nucleus which is made possible by the physical stress.

The invention also relates to suppressive monocyte derived cells, which present the following characteristics:

increased release, with respect to normal monocyte derived cells, of at least one of the following compounds:
prostaglandins such as PGE-2
arachidonic acid metabolites
TGE-β
V-EGF
IL-10
IL-4 and decreased level, with respect to normal monocyte derived cells, of expression and secretion of inflammatory and immunostimulating cytokines such as IL-1, IL-12, IFNγ, and decreased presence, on their membrane, with respect to normal monocyte derived cells of at least of the following activation or accessory molecules such as CD80, CD86, CD1a and adhesins such CD40 or ICAM, MHCI and MHCII molecules, and possibly decreased phagocytosis capacity with respect to normal monocyte derived cells and absence or inhibition of stimulation of T allogenic lymphocytes proliferation.

This can be determined according to "Suppression of Alloantigen-Induced T cell Proliferation by CD14" cells derived from granulocyte colony stimulation factor-Mobilized peripheral blood mononuclear cells" Mielcarek, Martin, Torok-Storb. Blood 89:1629–1634, 1997.

The invention also relates to suppressive monocyte derived cells according as described above, which present the following characteristics:

increased release, with respect to normal monocyte derived cells, of at least one of the following compounds:
prostaglandins such as PGE-2
arachidonic acid metabolites
TGF-β
V-EGF
IL-10
IL-4 and decreased level, with respect to normal monocyte derived cells, of expression of and secretion of inflammatory and immunostimulating cytokines such as IL-1, IL-12, IFNγ, and decreased presence, with respect to normal monocyte derived cells, on their membrane of at least one of the following activation or accessory molecules such as CD80, CD86, CD1a and adhesins such CD40 or ICAM, MHCI and MHCII molecules, and possibly decreased phagocytosis capacity, with respect to normal monocyte derived cells, and absence or inhibition of stimulation of T allogenic lymphocytes proliferation, and presence in their nucleus of at least one exogenous nucleic acid which has been integrated in the absence of the monocyte derived cell division.

The invention relates more particularly to suppressive monocyte derived cells, which present the characteristic of having integrated at least one exogenous nucleic acid in their nucleus in the absence of the monocyte derived cell division.

It is to be reminded that transfer of exogenous nucleic acids in cell nucleic by non viral techniques can be effectively achieved in rapidly dividing cells. In non dividing cells such as those derived from monocytes, the exogenous nucleic acids are internalized in vacuoles or in the cytoplasm, but very low integration in nucleic and expression of the coded peptide occur (<5%). The physical stimulation of the invention allows migration of the exogenous nucleic acids internalized from the cytoplasm to the nucleus and therefor enables increased expression to the transgene.

The invention also relates to a process for the preparation of suppressive monocyte derived cells comprising the step of inhibition of monocyte derived cells by physical means such as: UVA or UVB irradiation, α or β or γ irradiations, and/or electropulsation.

In a particular embodiment of the invention, the physical irradiation of mononuclear cells is performed during extracorporal circulation.

Irradiation is applied between 50 and 500 Gy, as described in "Effect of 60Co γ-irradiation on the nonspecific cytotoxicity of alveolar macrophages in vitro" (Yifen G., Lianping H. and Dechang W.; Env. Health Persp. 97:167, 1992).

The ultra-violet irradiation can be applied as described in "Reduced IL-12 production by monocytes upon ultraviolet-B irradiation selectively limits activation of T helper-1 cells" Kremer, Hilkens, Sylva-Steenland et al., J. Immunol. 157:1913–1918, 1996; or in "Ultraviolet B radiation sensitizes a murine epidermal dendritic cell Line (XS52) to undergo apopotosis upon antigen presentation to T cells". Kitajima, Ariizurni, Bergstresser and Takashima. J. Immunol. 15;:3312–3316, 1996).

Electropulsation (for instance 5 to 10 square electric pulses of 5 millisec at 0.3 to 0.8 kV/cm) allows flux of ions and of nucleic acids and/or protein transporters from the cytoplasm through the nucleus pores. This positive flux is stopped after the pulsation and the exogenous nucleic acid is integrated in nuclear DNA ("Specific electropermeabilization of leucocytes in a blood sample and application to large volumes of cells"; S. Sixou and J. Teissié; Elsevier, Biochimica et Biophysica Acta. 1028:154–160, 1990; "Control by pulse Parameters of Electric Field-Mediated Gene Transferin Mammnalian Cells", H. Wolf, M. P. Rois, E. Boldt, E. Neumann and J. Teissié, Phiophysical Journal, 66:524–531, 1994).

An advantageous process for preparing the suppressive monocyte derived cells of the invention, comprises the following steps of:

preparation of monocyte derived cells according to the following method
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceeding steps for instance by centrifugation (to remove 90% of platelets, red blood cells and debris) to obtain mononuclear cells;
3) resuspension of the total mononuclear cells (monocytes+lymphocytes) obtained at the preceeding step in culture medium (AIM-V, RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
inhibition of said monocyte derived cells by physical means such as: UVA or UVB irradiation, $\alpha$ or $\beta$ or $\gamma$ irradiations, for a time sufficient to induce the above-mentioned characteristics.

It should be noted that the step of inhibition of the monocyte derived cells can be achieved by chemical agents, which are able to induce changes on the monocyte derived cells, as defined above. In particular, the chemical means which can be used are anti-inflammatory drugs such as corticosteroids, non steroidal anti-inflammatory drugs or antioxidants (type nordihydroguaiaretic acid) or cytokine inhibitors such as cyclosporine, or ligands for inhibitory receptors specific for MHC-class I molecules.

The invention also relates to a process for the preparation of suppressive monocyte derived cells, comprising the following steps of:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceeding steps for instance by centrifugation (to remove 90% of platelets, red blood cells and debris) to obtain mononuclear cells;
3) resuspension of the total mononuclear cells (inonocytes+lymphocytes) obtained at the preceeding step in culture medium (AIM-V, RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
inhibition of said monocyte derived cells by addition of anti-inflammatory drugs such as steroids, particularly corticoids such as prednisone, dexamethasone, or of non steroid anti-inflammatory drugs such as indomethacine, sulindac, proxicam, ibuprofen, or of inhibitors of cytokines such as cyclosporine or tacrolimus, or of antioxidants such as nordihydroguaiaretic acid, or of ligands for inhibitory receptors specific for MHC-class I molecules.

It should be noted that the presence of contaminating lymphocytes with the monocytes derived cells during culture and differentiation of the monocytes allows a better control of suppressing and cell recovery through paracrine cellular interactions.

The lymphocytes can be segregated from the suppressive monocytes derived cells at the end of the process.

In a particular embodiment of the invention, the suppressive physical stress of mononuclear cells is performed during extracorporal circulation.

According to an advantageous embodiment of the invention, the step of preparation of the monocyte derived cells before inhibition can be carried out as described in patents PCT/EP93/01232, WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159:29–38, 1993);

"Immune therapy with macrophages: Present status and critical requirements for implementation" (Bartholeyns J., Romet-Lemonne J-L., Chokri M., Lopez M.; Immunobiol., 195:550–562, 1996);

"Dendritic cells can present antigen in vivo in a tolerogenic or immunogenic fashion" Finkelman, Lees, Birnbaum et al., J. Immunology, 157:1406–1414, 1996;

"Dendritic cells as adjuvants for immune-mediated resistance to tumors" (Schuler G. and Steinman R. M.; J. Exp. Med., 186:1183–1187, 1997).

The invention relates to a process for the preparation of suppressive monocyte derived cells as described above, comprising before the step of inhibition, the step of culture of said monocyte derived cells and contaminating lymphocytes for 2 to 24 h, in the presence of drugs, proteins or antigens to interiorize these compounds in said monocyte derived cells.

In a particular embodiment of the invention, the process described above comprises, prior to the step of stimulation, a step of loading the monocyte derived cells with exogenous compounds such as drugs, proteins, growth factors of interest (e.g. by pinocytosis, phagocytosis of particular aggregates, diffusion), or with DNA coding for a protein of interest for which specific induction of immunotolerance is required (i.e. with DNA plasmids, by sugar receptors mediated uptake for glycosylated polylysine-DNA or by lipid-DNA intake). The loaded monocyte derived cells are then stimulated by physical means such as described above, and more particularly by electropulsation which causes the transport of the exogenous compound loaded from the cytoplasm to the nuclei (where they can for example insert in DNA).

The invention also relates to a process for the preparation of suppressive monocytes derived cells as described above, comprising, after the step of inhibition, the additional step of:

centrifugation of the suppressive monocyte derived cells at a temperature enabling cell preservation, in particular at 4° C., and resuspension, for instance in isotonic medium containing autologous serum, to obtain a suspension of suppressive monocyte derived cells.

The invention also relates to a process for the preparation of suppressive monocytes derived cells as described above, comprising, after the step of inhibition, the additional steps of:

centrifugation of the suppressive monocyte derived cells at a temperature enabling cell preservation, in particular at 4° C., and resuspension, for instance in isotonic medium containing autologous serum, to obtain a suspension of suppressive monocyte derived cells, and freezing at a temperature of at least −80° C. aliquots of the suppressive monocyte derived cells obtained at the preceeding step, with the addition of a cryopreservative such as polyethyleneglycol, glycerol or DMSO.

The invention also relates to a process for the preparation of suppressive monocyte derived cells, comprising the following steps loading the monocyte derived cells thus obtained with an exogenous nucleic acid through endocytosis targeting their mannose and/or Fc receptors, or via pinocytosis of macromolecular nucleic acid aggregates, and submission of the monocyte derived cells obtained at the preceeding step to electropulsation enabling intracellular transfer of the exogenous nucleic acid into the nucleus and integration into the DNA of the nucleus, for example of about 1 to about 10 pulses of about 5 msecs at about 0,3 to about 1 kV/cm.

The invention also relates to a process for the preparation of suppressive monocyte derived cells, comprising the following steps:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceeding steps for instance by centrifugation (to remove 90% of platelets, red blood cells and debris) to obtain mononuclear cells;
3) resuspension of the total mononuclear cells (monocytes+lymphocytes) obtained at the preceeding step in culture medium (RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;

loading the monocyte derived cells thus obtained with an exogenous nucleic acid through endocytosis targeting their mannose and/or Fc receptors, or via pinocytosis of macromolecular nucleic acid aggregates, submission of the monocyte derived cells obtained at the preceeding step to electropulsation enabling intracellular transfer of the exogenous nucleic acid into the nucleus and integration into the DNA of the nucleus.

The invention also relates to a process for the preparation of suppressive monocyte derived cells as described above, comprising before the step of loading, the step of culture of said monocyte derived cells and contaminating lymphocytes for 2 to 24 h, in the presence of drugs, proteins or antigens to interiorize these compounds in said monocyte derived cells.

The invention also relates to a process for the preparation of suppressive monocytes derived cells as described above, comprising, after the step of electropulsation, the additional step of:

centrifugation of the suppressive monocyte derived cells at a temperature enabling cell preservation, in particular at 4° C., and resuspension, for instance in isotonic medium containing autologous serum, to obtain a suspension of suppressive monocyte derived cells.

The invention also relates to a process for the preparation of suppressive monocytes derived cells as described above, comprising, after the step of electropulsation, the additional step of:

centrifugation of the suppressive monocyte derived cells at a temperature enabling cell preservation, in particular at 4° C., and resuspension, for instance in isotonic medium containing autologous serum, to obtain a suspension of suppressive monocyte derived cells, freezing at a temperature of at least −80° C. aliquots of the suppressive monocyte derived cells obtained at the preceeding step, with the addition of a cryopreservative such as polyethyleneglycol.

The invention also relates to suppressive monocyte derived cells such as obtained by the process as described above.

The invention also concerns a pharmaceutical composition comprising, as active substance, suppressive monocyte derived cells as described above, in association with a pharmaceutically acceptable vehicle.

The invention is also related to a pharmaceutical composition as described above, in the form of sterile injectable preparations.

In the injectable preparation, the active substance is present in an amount such that it corresponds from about $10^7$ to about $10^{10}$ cells/kg of body weight, particularly from about $10^8$ to about $10^9$. In a topical preparation, the active substance is present in an amount of about $10^5$ to about $10^8$ cells/cm$^2$ of body surface.

In a particular embodiment, the monocyte derived cells are injected repeatedly at doses of $10^7$ to $5.10^9$ at intervals of 3 days to 6 months.

The injections can be first local (subcutaneous, intramuscular, mucosal or in tissues) and then systemic (intravenous or intralymphatic).

The invention also relates to a pharmaceutical composition, in the form of a immunotolerant composition comprising, as active substance, suppressive monocyte derived cells as described above, having integrated in their nucleus an exogenous nucleic acid coding for a polypeptide or protein for which tolerance is desired.

The invention is also related to the use of monocyte derived cells with immunosuppressive properties as described above, for the preparation of a medicament for inducing immunotolerance or for treating autoimmunity, chronic inflammations or allogenic graft rejection or for treating polypeptide or protein deficiency in a patient, said use comprises the preparation of sterile flasks of monocyte derived cells with immunosuppressive properties suspension and there repeated local or systemic administration.

The invention also relates to a method for inducing immunotolerance comprising the use of a suppressive monocytes derived cells as described above.

The invention also concerns a method for inducing specific immunotolerance, wherein said suppressive monocytes derived cells has integrated in its nucleus an exogenous nucleic acid coding for a polypeptide or a protein for which tolerance is desired.

The invention is also related to a method for treating autoimmunity, chronic inflammations or allogenic graft rejection, comprising the use of suppressive monocytes derived cells as described above.

The invention also relates to a method for ex vivo gene therapy comprising the use of suppressive monocyte derived cells as described above, with said suppressive monocyte derived cells having integrated in their nucleus an exogenous nucleic acid coding for a polypeptide or a protein which is deficient in a patient.

The invention relates to a method for the inhibition of MDC comprising the preparation of suppressive MDC as described above and the injection in vivo to a patient to induce immunotolerance as evidenced by cytokine profile and biological effects.

The invention will be further illustrated in the following detailed description.

Ex vivo stressing of monocytes derived cells (MDC) by physical treatment to induce a new desired biological activity.

Human blood derived mononuclear cells are grown ex vivo in culture bags in defined medium. They are submitted to specific stimuli such as UVA radiation electropulsation, and $-\alpha$, $-\beta$, $-\gamma$ irradiation. The intensity and length of these treatments determines the physiological status achieved by the MDC (Monocytes Derived Cells).

Before physical treatment, the differentiated MDC have eventually phagocytosed specific compounds such as drugs, nucleic acids, polypeptides, chemokines or growth factors, and are loaded with these compounds to be processed and/or released when required. They have therefore gained ex vivo new specific potential that can then be exploited therapeutically by local or systemic reinjection to the patient from whom the original blood mononuclear cells were aphorized. Thus the release of various factors artificially loaded or endogenously produced by stressed MDC which are themselves in a suppressive status, is controlled.

Methods and culture conditions are disclosed describing the physical treatments used and the specific MDCs functionalities obtained. The beneficial suppressive regulatory effects achieved by these cells after adoptive transfer to treat diseases (i.e. inflammatory or auto-immune) is described.

Monocytes-Macrophages or Macrophages-Dendritic cells MDCs), grown ex vivo, are subsequently exposed to UVA or gamma irradiation, for purpose of gaining new therapeutic inhibitory potential—generally via controlled release of various factors either artificially loaded into or endogeneously produced by MDCs.

Monocytes derived cells can be obtained in large amounts ($>10^9$ MDCs) after culture of total mononuclear cells including lymphocytes obtained from blood apheresis or from blood "buffycoats" containing peripheral blood leukocytes in plastic or hydrophobics bags (for example ethylene vinyl acetate or Teflon) and in defined culture media (see PCT patent application No. PCT/FR96/00121).

These MDCs are differentiated after one week of culture. They are then exposed in vitro to physical stress.

In the present invention, the stress consists in the disturbance caused by UVA or UVB radiation, or $-\alpha$, $-\beta$ and $-\gamma$ irradiation, and electropulsation which results in temporary modification of ion fluxes, and as a result, flux of molecules (proteins, drugs, nucleotides or nucleic acids from the cytoplasm to the nucleus. As a result, the stressed MDCs are suppressed. The suppressed MDCs have acquired new characteristics as described above.

Three examples of ongoing developments and applications are described hereafter.

a) In a particular embodiment of the invention, MDCs are obtained according to the procedures of the art (N.B.: they are not activated by FN$\gamma$ or other activators and no cyclooxygenase inhibitor is present in the culture or taken by the blood donor).

The cells are submitted to 30 min. UVA–UVB irradiation

The suppressive property of these cells is demonstrated by the fact that when they are added in vitro to allogenic lymphocytes, they inhibit the proliferation of T lymphocytes (inhibition of mixed lymphocyte reaction test).

These stressed "suppressed" MDCs injected to rodents with chronic inflammatory disease such as rheumatoid arthritis are found to inhibit the inflammatory symptoms.

In this case, the MDCs with immunosuppressive properties are obtained after UV exposure. UVA or UVB of 1 to 2 Joules/cm$^2$ of intensity is applied to mononuclear cells ($10^6$/ml in RPMI medium) in EVA plastic bags. The MDCs obtained present low amount of costimulatory molecules (MHC, CD40, B7 . . . ) on their membranes, they release prostaglandins and inhibit the proliferation of T lymphocytes in mixed lymphocyte reactions. The clinical effect on patients with chronic rheumatoid arthritis is studied after injection of autologous suppressive macrophages previously submitted to UV radiations.

b) In a second embodiment of the invention, the MDCs are loaded during 4 h at 37° C. with 0.1 $\mu$g/ml of polylysine cDNA coding for an antigen (myelin) implicated in an auto-immune reaction. The cells are then stressed by UV (30 min. at 1 joule/cm$^2$) and electropulsation (5 square electric pulses of 5 millisec at 0.8 kV). The stressed "suppressed" MDCs are then presenting on their membrane epitopes of the antigen involved in an auto-immune reaction; myelin basic protein as evidence by FACS analysis (fluorescence cell analysis). Absence of stimulation (proliferation) of specific T cytotoxic cells and lack of inflammatory signal coexpressed (FACS analysis) demonstrates that the MDCs are tolerogen for the antigen presented. In vitro, these stressed suppressive MDCs inhibit the T lymphocyte proliferation to the antigen (myelin). In rodents experimental models of encephalomyelitis, the systemic transfer of stressed MDCs presenting myelin epitopes in a suppressive environment, is used to measure their effect on the progression of auto-immunity.

c) In a third embodiment of the invention, MDCs are loaded with nucleic acids through endocytosis targetting their mannose receptors, or via pinocytosis of macromolecular nucleic acid aggregates. These cells are then submitted to short electropulsation stimuli allowing intracellular transfer of the nucleic acid into the cell nuclei and integration in DNA. These cells are then washed and injected in animal models where they express for several weeks and release locally the polypeptides coded by the nucleic acids interiorized before ex vivo physical treatment.

Conditions for uptake of polylysine-cDNA were 40 $\mu$g/ml/$10^8$ cells for 1 h at 37° C., followed by 5 to 10 electric pulses of 5 millisec at 0.3 to 0.8 kv.

The effective transfection ($\geq$10% efficiency and high intensity of expression) allows prolonged expression and release of the protein of interest in the extracellular medium, as measured by ELISA.

This technique proves particularly useful in the long lasting replacement of genetic deficiencies such as Factor IX in haemophiliacs with Factor IX deficiency without induction of anti-FIX auto-antibodies due to selective immunosuppression to F-IX.

MDCs injected in an autologous way in patients survive for several months in tissues where they release the deficient protein or factor of therapeutic interest.

In this particular embodiment of the invention, the MDCs obtained after one week of culture have been loaded by sugar receptors mediated uptake for glycosylated polylysine-DNA. The MDCs are then exposed to the physical stress (i.e. electropulsation which causes the transport of the compounds loaded from the cytoplasm into the nuclei where they can for example insert in DNA).

In a forth embodiment of the invention, dendritic cells from C57BL/6 mice are derived from bone marrow using IL-13 and GM-CSF and are treated in the culture medium during differentiation with 0.025 mg/ml hydrocortisone.

C57BL/6 mice transgenic for the lymphocytic choriomeningitis virus glycoprotein (LCMV-GP) under the control of the rat insulin promoter (RIP) express the GP antigen on the pancreatic beta cells of the Langerhans islets.

When such mice are infected with LCMV virus or vaccinated with untreated DC loaded with the immuno dominant epitope (GP33.41) derived from the LCMV-GP, a massive infiltration of the pancreas is observed, and mice develop autoimmune diabetes. To evaluate the efficacy of chemically induced suppressive DCs as vaccine, transgenic mice are injected with hydrocortisone treated DCs loaded with the same peptide; a strong infiltration is observed in the pancreas but no diabetes occurs. Analysis of the cell infiltrate reveals mainly Th2 type cytokine secretion. Moreover, when these vaccinated mice are further infected with LCMV, no diabetes is observed, indicating that the mice are protected against the induction of the disease.

What is claimed is:

1. Monocyte derived cells which have immunosuppressive properties presenting the following properties:
   increased the release, with respect to normal monocyte derived cells, of at least one of the compounds selected from the group consisting of PGE-2, IL-10 and IL-4,
   and decreased the level of expression and secretion of at least one of the inflammatory and immunostimulating cytokines selected from the group consisting of IL-1, IL-12, and IFNγ, with respect to normal monocyte derived cells,
   and decreased the presence, on their membrane, with respect to normal monocyte derived cells, of at least one of the accessory molecules selected from the group consisting of CD80, CD86, and CD40,
   and having polylysine-cDNA encoding of myelin protein integrated into the cell nucleus.

2. The monocyte derived cells, with immunosuppressive properties, according to claim 1, wherein the increased release, with respect to normal monocyte derived cells, of at least one of the compounds selected from the group consisting of PGE-2, IL-10 and IL-4 is in an amount higher than 0.1 pg/cells/hr.

3. The monocyte derived cells, which have immunosuppressive properties, according to claim 1, wherein the decreased level, with respect to immature dendritic cells, macrophages or monocyte derived cells, of expression of and secretion of inflammatory and immunostimulating cytokines selected from the group consisting of IL-1, IL-12 and IFNγ is below 0.01 pg/cell/hr.

4. The monocyte derived cells, which have immunosuppressive properties, according to claim 1, wherein the decreased presence, with respect to normal monocyte derived cells, on the membrane of at least one of the following activation or accessory molecules selected from the group consisting of CD80, CD86, CD40, MHC class I and MHC class II molecule in an amount of less than $10^3$ molecules per cell.

5. A pharmaceutical composition comprising, monocyte derived cells which have immunosuppressive properties according to claim 1, in association with a pharmaceutically acceptable vehicle.

6. The pharmaceutical composition according to claim 5, in the form of sterile injectable preparations.

7. The pharmaceutical composition, in the form of an immunotolerant composition comprising, as an active substance, monocyte derived cells which have immunosuppressive properties according to claim 5, having integrated in their nucleus a polylysine-cDNA coding for which tolerance is desired.

8. The monocyte derived cells, which have immunosuppressive properties, according to claim 1, which present the following properties:
   having polylysine-cDNA encoding for a myelin protein which has been integrated into the nucleus of said monocyte derived cell in the absence of cell division.

* * * * *